(12) United States Patent
Berger et al.

(10) Patent No.: US 6,561,767 B2
(45) Date of Patent: May 13, 2003

(54) CONVERTING A PUMP FOR USE IN SUPERCRITICAL FLUID CHROMATOGRAPHY

(75) Inventors: Terry A. Berger, Newark, DE (US); Kimber D. Fogelman, Hockessin, DE (US); L. Thompson Staats, III, Lincoln University, PA (US); Mark Nickerson, Landenburg, PA (US); Paul F. Bente, III, Landenburg, PA (US)

(73) Assignee: Berger Instruments, Inc., Newark, DE (US)

( * ) Notice: Subject to any disclaimer, the term of this patent is extended or adjusted under 35 U.S.C. 154(b) by 0 days.

(21) Appl. No.: 09/918,436

(22) Filed: Aug. 1, 2001

(65) Prior Publication Data

US 2003/0026704 A1 Feb. 6, 2003

(51) Int. Cl.[7] .......................... F04B 19/24; F04B 23/00; F04B 49/00
(52) U.S. Cl. .......................... 417/53; 417/313; 417/279
(58) Field of Search .......................... 417/53, 313, 279; 73/19.02

(56) References Cited

U.S. PATENT DOCUMENTS

| 4,373,864 A | * | 2/1983 | Massey et al. | 417/213 |
| 5,089,124 A | * | 2/1992 | Mahar et al. | 210/101 |
| 5,281,406 A | * | 1/1994 | Stalling et al. | 423/455 B |
| 5,305,232 A | * | 4/1994 | Chimowitz et al. | 210/386 |

OTHER PUBLICATIONS

"chromatography" Encyclopedia Britannica <http:www.search.eb.com/eb/article?eu=119265>.*

* cited by examiner

Primary Examiner—Charles G. Freay
Assistant Examiner—Timothy P. Solak
(74) Attorney, Agent, or Firm—ZITO tlp; Joseph J. Zito; Kendal M. Sheets

(57) ABSTRACT

A method for converting a pump for use in a flow stream containing a mixture of highly compressed gas, compressible liquid or supercritical fluid wherein the pump delivers a compressible fluid against a back-pressure regulator which in turn delivers a controllable flow rate downstream of the regulator without performing variable compressibility compensation adjustments on the pump. By using a pressurized source of compressible fluid combined with isocratic conditions, the delivery pressure from the pump is controlled at a rate higher than the downstream gradient with the back-pressure regulator, and an inexpensive pump may be used in place of specialized, expensive pumps and compressibility compensation systems for use in stems operating at or near supercritical fluid levels of compressible fluids. Significant capital and operating laboratory costs are saved through a simpler and cheaper system for accurately delivering compressible fluids into mobile phase flow streams.

12 Claims, 2 Drawing Sheets

CONVERTING A PUMP FOR USE IN SUPERCRITICAL FLUID CHROMATOGRAPHY

BACKGROUND OF THE INVENTION

Pumps used in SFC Supercritical Fluid Chromatography control the mass-flow of each component of the mobile phase, and therefore control the composition of the mobile phase through the column. Pumping compressible fluids, such as carbon dioxide (CO2), at high pressures in SFC systems while accurately controlling the flow, is more difficult than that for a liquid chromatography system. SFC systems use two pumps to deliver two different source streams into a single mobile phase flow stream. Each pump on each flow stream adds pressure, flow ripples, and variances that cause baseline noise. The two pumps also operate at different frequencies, different flow rates, and require separate compressibility compensations, further adding to the complexity of flow operations.

Pumps used for supercritical fluid chromatography typically require an extended compressibility compensation range plus a dynamically variable compressibility compensation range to accurately deliver a desired flow rate and fluid composition. When a compressible fluid is mixed with an incompressible fluid, the viscosity of the mixture depends on the mole fraction of the modifier, or incompressible fluid, in the compressible fluid. In combi-chem analysis and purification by SFC, the concentration of modifier can be varied from 2.5 to 55% over a few minutes. This can result in a major change in the viscosity of the fluid and in the pressure drop across a chromatographic column that can change over an order of magnitude from approximately 9 bar to greater than 250 bar.

Normally, an unmodified high performance liquid chromatography (HPLC) pump would deliver an unknown and varying amount of a compressible fluid under such conditions. As the column head pressure increases during the gradient, a larger percentage of each pump stroke would be used up compressing the fluid instead of delivering flow. With an uncompensated pump, the delivery rate becomes a smaller fraction of the flow setpoint. When a second pump is added to a system to deliver an incompressible fluid under high pressure, its delivery rate is unaffected by the increasing pressure. Subsequently the two pumps deliver inaccurate flow and composition to the mobile phase. As the pressure in the system rises, the total flow drops below its setpoint, but the concentration of the modifier increases beyond the modifier setpoint. The temperature of the compressible fluid in the pump head must be controlled to prevent the delivered mass flow from changing even further.

When compressed, a pumping fluid heats up and attempts to expand. For highly compressible carbon dioxide at outlet pump pressures above 200 bar, temperature rise of more than ten degrees centigrade are possible within the fluid. The rapid compression of the pumping fluid causes the fluid to heat up and expand and the density to decrease. When heat is transferred to the pump body, the pumped fluid cools and the fluid density increases.

Reciprocating pumps are typically used in HPLC and SFC. These pumps are more accurate than syringe pumps and can deliver essentially an infinite volume before refilling. A reciprocating pump has an inlet and outlet check valve. During a fill stroke, the outlet check valve closes, isolating the pump from the high pressure in the downstream column ($P_{col}$). The pressure from a filling cylinder of source fluid, such as compressed CO2, ($P_{cyl}$) forces open the inlet check valve and fills the pump chamber. After the pump is filled at $P_{cyl}$, the piston reverses direction, compressing the fluid in the pump until $P_{pump} > P_{cyl}$, which closes the inlet valve. On the compression stroke, the piston moves rapidly until $P_{pump} > P_{col}$ at which point the outlet valve opens and the fluid moves downstream of the pump and into the column. The piston slows down to the delivery speed when enough extra fluid has been pushed into the column to compensate for lack of flow during the fill stroke. The distance the piston must travel just to compress the fluid to $P_{col}$ is calculated based on the known volume of the components and a characteristic of the fluid being pumped, called the compressibility factor Z. With the correct Z, a pump can be controlled to nearly eliminate flow or pressure ripple.

Without a correct Z, the pump either under- or over-compresses the fluid causing characteristic ripples in flow and pressure. Either under- or over-compression results in periodic variation in both pressure and flow with the characteristic frequency of the pump (ml/min divided by pump stroke volume in ml). The result is noisy baselines and irreproducibility. To compensate for this, the more expensive and better liquid chromatography pumps have compressibility adjustments to account for differences in fluid characteristics.

High-pressure SFC pumps have an extended compressibility range and the ability to dynamically change the compression compensation. While these pumps are used as flow sources and the pressure and temperature of the delivered fluid may be measured. The pumps can change the length of compression to account for changes in compressibility with pressure and temperature. Methods in the prior art calculate ideal compressibility based on measured temperature and pressure using a sophisticated equation of state. The method then uses dithering around the setpoint to see if a superior empirical value can be found. This approach is described in U.S. Pat. No. 5,108,264, Method and Apparatus for Real Time Compensation of Fluid Compressibility in High Pressure Reciprocating Pumps, and U.S. Pat. No. 4,883,409, Pumping Apparatus for Delivering Liquid at High Pressure. Other prior art methods move the pump head until the pressure in the refilling cylinder is nearly the same as the pressure in the delivering pump head. One method in U.S. Pat. No. 5,108,264 Method and Apparatus for Real Time Compensation of Fluid Compressibility in High Pressure Reciprocating Pumps, adjusts the pumping speed of a reciprocating pump by delivering the pumping fluid at high pressure and desired flow rate to overcome flow fluctuations. These are completely empirical forms of compressibility compensation. The prior art methods require control of the fluid temperature and are somewhat limited since they do not completely compensate for the compressibility. The compensation stops several hundred psi from the column inlet pressure.

The compressibility of the pumping fluid directly effects volumetric flow rate and mass flow rate. These effects are much more noticeable when using compressible fluids such as carbon dioxide in SFC rather than fluids in liquid chromatography. The assumption of a constant compressibility leads to optimal minimization of fluid fluctuation at only one point of the pressure/temperature characteristic, but at other pressures and temperatures, flow fluctuations occur in the system.

If the flow rate should be kept as constant as possible through the separation column. If the flow rate fluctuates, variations in the retention time of the injected sample would occur such that the areas of the chromatographic peaks produced by a detector connected to the outlet of the column would vary. Since the peak areas are representative for the concentration of the chromatographically separated sample substance, fluctuations in the flow rate would impair the accuracy and the reproducibility of quantitative measurements. At high pressures, compressibility of solvents is very noticeable and failure to account for compressibility causes technical errors in analyses and separation in SFC.

SUMMARY OF THE INVENTION

The invention relates to a method and apparatus for converting a pump for use in a combined flow stream containing a mixture of highly compressed gas, compressible liquid or supercritical fluid; and a relatively incompressible liquid. In particular, the invention pertains to converting a pump with a constant compressibility compensation for use in gradient elution supercritical fluid chromatography (SFC).

The problem addressed by the present invention is how to accomplish accurate composition of a flow stream and steady flow rates while avoiding variable compression compensation adjustments to a flow pump that is delivering a highly compressible fluid, such as carbon dioxide, to a supercritical fluid chromatography class of system. In the present invention, unmodified HPLC pumps can to deliver reproducible flow conditions of a pure fluid under isocratic conditions to an SFC system, despite having limited compressibility compensation ranges and no ability to dynamically compensate for compressibility changes. The pump delivers a compressible fluid against a back-pressure regulator installed just downstream of the pump's outlet, thereby holding a pressure force against the pump and delivering a steady, high pressure flow stream to a separation column. Pressures can reach upwards of approximately 600 bar in the flow stream. The result of the invention is controllable flow of a compressible fluid delivered downstream of the regulator to the mobile phase and into the SFC column without performing dynamic compression compensation or other types of compensations for leaks and ripples in flow on the pump.

In the present invention, calculating variable compressibility compensation is avoided when pumping compressible fluids in a supercritical fluid chromatography system. Normally a pump has to change the nature of how it moves to compress fluids, and once the fluid is compressed, then the pump delivers the fluid. The hardware and methods for performing precise compressibility in laboratory-scale pumps are difficult and expensive. By using a relatively inexpensive pump without precise mechanics, outlet pressure is controlled with the current invention, thereby significant reducing capital and operating laboratory costs. Pressure downstream of the back pressure regulator 12 may vary according to the dynamics of the SFC system. However, the pressure delivery out of the pump 10 is a constant delivery to the system.

A back pressure regulator is mounted just downstream of the pump in a supercritical chromatography system and controls the pump's outlet pressure above the inlet pressure, while maintenance pressure drop across the pump constant. The back pressure regulator could be mechanical, or electromechanical, or thermally controlled. Any of the types of back pressure regulators work with the preferred embodiment. The density of the fluid in the pump varies over a carefully controlled range during refill and delivery. If the inlet pressure is relatively high the fluid is less compressible. If the temperature of the fluid is then maintained constant, sub-ambient level, the fluid is still less compressible and there is no change in the compressibility during a run. In an alternative exemplary embodiment, a separate system could pre-pressurize the fluid entering the pump to an elevated pressure.

In an alternative exemplary embodiment, a separate system could pre-pressurize the fluid entering the pump to an elevated pressure. A back pressure regulator is mounted just downstream of the pump and controls the pump's outlet pressure above the inlet pressure, while maintaining the pressure drop across the pump constant. The density of the fluid in the pump varies over a carefully controlled range during refill and delivery. If the inlet pressure is relatively high the fluid is less compressible. If the temperature of the fluid is then maintained constant, sub-ambient level, the fluid is still less compressible and there is no change in the compressibility during a run.

BRIEF DESCRIPTION OF THE DRAWINGS

For a better understanding of the nature of the present invention, reference is had to the following figures and detailed description, wherein like elements are accorded like reference numerals, and wherein.

DETAILED DESCRIPTION OF PREFERRED EXEMPLARY EMBODIMENT

Figure 1:
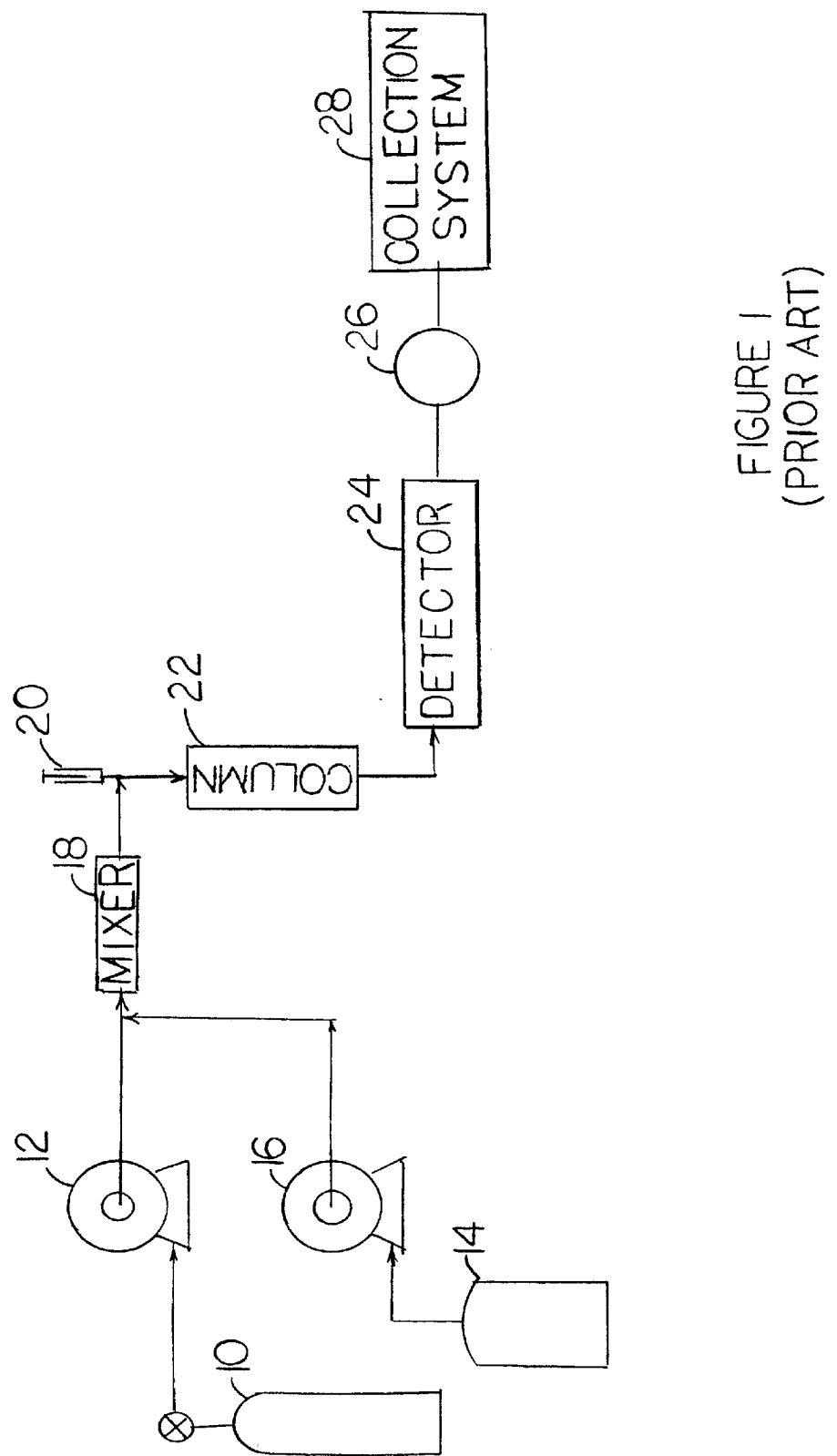
FIG. 1 illustrates a schematic flow diagram of the supercritical fluid chromatography system in the prior art.

The method of operation of the present invention is particularly applicable to a supercritical fluid chromatography system (SFC) depicted in the schematic of prior art in FIG. 1. The system has a reservoir supply tank 10, holding a liquefied compressed gas, such as carbon dioxide ($CO_2$). The reservoir feeds into a high-pressure mass flow control pump 12, which adds a compressible fluid 10 to the flow stream. The SFC system has a second reservoir tank 14, which contains modifier solvent, such as methanol, for the purpose of producing binary mixtures of modifier dissolved in the $CO_2$ fluid. The modifier 14 feeds a corresponding high-pressure mass flow control pump 16, which adds the modifier to the combined mobile phase flow stream. The two streams combine downstream of the pumps 12,16 and enter a mixing column 18 under pressure, wherein the two streams mix more thoroughly to create a single flow stream at or near supercritical conditions. Downstream of the mixing column 18, an injection valve 20 adds sample into the flow stream.

Samples are typically injected into the mobile phase through a fixed-loop type of injector fed by a syringe or automated sample pump. After sample injection, the flow stream enters one or more chromatography columns 22. SFC systems may operate with either packed columns or capillary columns. The outlet of the column 22 feeds the inlet of a detection device 24 that produces the chromatogram. The outlet from a detector 24 passes through a back-pressure regulator valve 26 and from there to a suitable means for fluid recovery 28. The back-pressure regulator 26 controls the pressure throughout the column 22 such that the fluid passing from the outlet of the column 22 to the detector 24 remains at or near a desired fluid density and pressure. The method of holding high pressure in the system insures solvation throughout the entire column structure of the column or multiple columns.

The problem addressed by the present invention is how to accomplish reproducible flow and steady flow for a pure fluid under isocratic conditions in an SFC system while avoiding variable compression compensation adjustments to flow pump 12 that is pumping a highly compressed gas, compressible liquid or supercritical fluid. Pumps used for supercritical fluid chromatography require an extended compressibility compensation range plus a dynamically variable compressibility compensation range to deliver a controllable flow rate and fluid composition.

The method of the present invention permits unmodified HPLC pumps to deliver accurate flow composition under isocratic conditions, despite having limited compressibility compensation ranges and no ability to dynamically compensate for compressibility changes. The method controls both the inlet and outlet pressures of the pump delivering the compressible fluid. The outlet pressure is typically controlled at pressure much higher than the inlet pressure and higher than any pressure likely encountered in the subsequent use for chromatography. If the inlet pressure is constant, the fluid inlet temperature is constant, and the pressure difference across the pump is held constant, then there is no change in compressibility of the fluid. The pump can be operated at low flow rates or high flow rates and the mass flow delivered is a function of displacement speed of the piston. This approach circumvents the main problem in making accurate flow and composition in SFC due to compressibility compensation problems.

Figure 2:
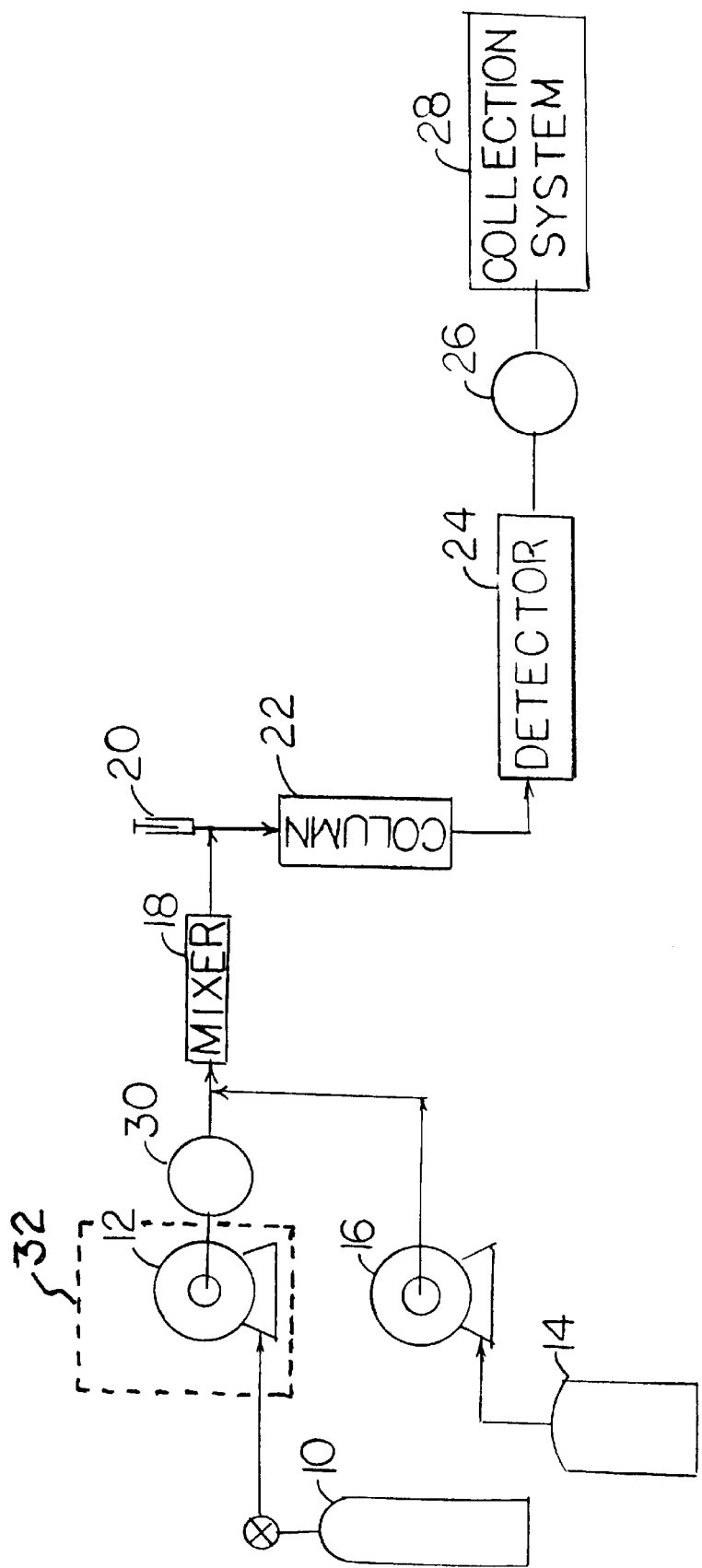
FIG. 2 illustrates a schematic diagram of the modification of the system in FIG. 1 modified by the inclusion of a pressure regulator in accordance with the principles of the present invention.

For implementation of an exemplary embodiment of the present invention, reference is made to FIG. 2. FIG. 2 is a schematic diagram from FIG. 1 with the addition of a back-pressure regulator 30 installed downstream of the pump 12 outlet. The back-pressure regulator 30 is set such that the pump 12 delivers compressible fluid 10 against at a fixed high pressure force. The pressure rate is set higher than the pressure at any point in the downstream gradient of the SFC system to ensure a steady flow regardless of pressure drops across a component. In such a mode of operation, the pump is used as a flow source. For example, the back-pressure regulator 30 could hold the pressure against the pump 12 at a constant 600 bar. The outlet pressure to the pump is not controlled, except for a second downstream back-pressure regulator 26 after the detector 24 that is set to a lower pressure, such as 100 bar. It is important to note that the pressure immediately from the pump 12 at its outlet is not controlled, rather the pump is pumping against a fixed back-pressure regulator to deliver a steady flow to column 22. The pressure drops downstream of the back-pressure regulator to whatever rate the system permits. The mass flow from the pump is controlled even though the flow rate is unknown. However, the flow rate out of the pump can be calibrated because the pump is operating at a speed, but the flow stream from the pump is leaving at a rate less than an ideal pump rate because energy is used compressing the fluid in the pump.

The present invention avoids the need for monitoring and updating high-pressure SFC pumps 12 for variable compressibility compensation. This method directly addresses the problem with methods and pumps in the prior art of SFC: as the pressure changes on the pump outlet, new compressibility compensations must be determined and the pump adjusted. Typically, pumping compressible fluids at or near SFC pressures requires that the pump must be monitored and adjusted to change the nature of how it compresses and delivers the fluid. This type of monitoring and adjustment in the SFC process is difficult and expensive.

The present invention does not require knowledge of the compressibility constant of the fluid being delivered to the chromatography system because the pump is pumping at constant pressure. The pump can run at different flowrates in an open loop with no compressibility compensation. The pump is controlled by the constant pressure and therefore flowrate may be changed independent of compressibility. If the pump is pumping at the same pressure, the flowrate and composition is controllable without the need for dynamic compressibility compensation. For example, the present invention does not require the calculation of how far to move the pumping pistons or how far to move the intake strokes. This is because the compressibility constant of a compressible fluid is always the same downstream of the back-pressure regulator 30. The system operates when the first flow stream is a "pure fluid." A "pure fluid" is one that is a single composition that follows a well-defined gas law. Examples of pure fluids used in SFC flow streams are carbon dioxide and freon. The pure fluid flow stream is also operated under isocratic conditions, keeping temperature and pressure as constant as is practicable.

An exemplary embodiment of the present invention could use a relatively inexpensive pump to deliver reproducible and controllable flow, without the close monitoring and adjustment typically required for SFC. Various types of pumps are also capable of delivering the flow, such as reciprocating, dual-piston, diaphragm and screw pumps. Because the pressure on the pump outlet is constant due to the back-pressure regulator 30, the same compressibility compensation is performed regardless of the flow. The flow may vary from the pump and the speed of the pump may change, but the pressure on the outlet of the pump remains constant. Therefore a different compressibility compensation scheme is not required when flow rate changes.

In a preferred embodiment, pressure is maintained downstream of the detector 24 by a second back-pressure regulator 26. The pressure on the downstream side of the first back-pressure regulator 30 can adjust to the system pressure as ultimately determined by the second back-pressure regulator 26 and pressure drops throughout the system. The pressure on the upstream side of the first back-pressure regulator 30 is higher than the pressure at the column 22 inlet to create a high pressure differential flowing towards the column. For example, the inlet pressure of the first regulator 30 may be set to approximately 300 bar and the pressure in the second regulator 26 may be set to approximately 100 bar. The higher pressure in the upstream regulator 30 creates a steady flow stream gradient to the column that is within variable flow rate and composition tolerances corresponding to the scale and flow rate demands of each sample run in the system. The flow stream becomes far less susceptible to compressibility compensation problems than prior art SFC methods.

Any of the types of back-pressure regulators capable of use in SFC systems work with the preferred embodiment. Back-pressure regulators 26, 30 may be either mechanically, electromechanically, or thermally controlled. However, back-pressure regulators should have low dead volumes if peak collection is an important result. Some older generation back-pressure regulators have low dead volumes as high as 5 ml. Back-pressure regulators may also be heated to prevent the formation of solid particles of the mobile phase as the fluid decompresses. These particles can cause noisy baselines and erratic flow within the system.

The supply stream compressible fluid 10 that is upstream of pump 12 should be pressurized. In an exemplary embodiment, steel or aluminum canisters 10 of CO2 can deliver pressurized flow to the inlet of the pump 12. To operate the method as close as possible to isocratic conditions, the temperature of the compressible fluid 10 should also be controlled by temperature regulator 32 to the extent practicable. After a compression stroke in the pump 12, the temperature of the fluid inside the pump rises. The compression stroke of the pump raises the temperature of the fluid by adiabatic heating. Temperature compensation 32 may be implemented on the fluid flow to the pump 12 by methods known in the prior art, such as chilling the pump heads, to control the temperature and pressure of the fluid on the outlet side of the pump 12. If the inlet pressure to the pump 12 is constant, the fluid inlet temperature is constant 32, and the pressure difference across the pump is held constant, then there are only minor changes in compressibility of the fluid. The result is that when the pump 10 is operated at either low or high flow rates, the mass flow delivered is a function of the displacement speed of the piston.

The lowest delivery pressure by the pump 12 against the first back-pressure regulator 30 may be much higher than the pressure of traditional SFC pumps. The higher delivery pressure also adds additional stress on piston seals which could cause premature wear and failure. The method of the present invention may also be less applicable for pressure or density programming of a pure fluid than a more traditional SFC pumping system, because both the lowest and highest pressures available may be limited. However, the method should be highly effective in the combi-chem application where the required range of total flow and a repetition of the same gradient can be accomplished using a narrower range of pressures.

An alternative exemplary embodiment utilizes a separate system that could pre-pressurize the fluid 10 entering the pump 12 to an elevated pressure. A back-pressure regulator is mounted downstream of the pump 12 in the similar position to 30 in FIG. 2, to control the pump outlet pressure above the inlet pressure while maintaining the pressure drop across the pump constant. If the inlet pressure from the fluid source 10 is relatively high, the fluid is less compressible. If the temperature of the fluid is then maintained at a constant, sub-ambient level, the fluid is less compressible and there is little change in compressibility of the fluid while the system is in full operation.

The present invention is well suited for use in chromatography systems operating in the supercritical, or near supercritical, ranges of flow stream components where it is necessary to obtain steady flow of liquid at high pressures with high degrees of accuracy of flow to a separation column or other separation device. Other applications include supercritical extraction systems or preparatory systems where separation and/or collection of sample components injected into a high-pressure flow streams occur.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed:

1. A method for converting a pump for use in a combined flow stream containing a mixture of highly compressed gas, compressible liquid or supercritical fluid; and a relatively incompressible liquid, comprising:

controlling pressure of a first flow stream containing a highly compressed gas, compressible liquid, or supercritical fluid, by maintaining an elevated pressure rate after said outlet of said pump but prior to joining a second flow stream of a relatively incompressible liquid;

pumping of said first flow stream consisting of a pure fluid resulting in delivery of a controllable flow rate of said first flow stream at a constant compressibility compensation without the need for dynamically compensating said pump for compressibility changes in said first flow stream.

2. The method of claim 1, wherein:

said maintenance of an elevated pressure rate after said outlet of said pump being accomplished by delivering said fluid first flow stream from said pump against a back pressure regulator valve installed in said first flow stream downstream of said pump and upstream to the joining of said first flow stream with said second fluid flow stream containing a relatively incompressible liquid.

3. The method of claim 2, further comprising the step of:

determining the mass flowrate of said first flow stream after said back-pressure regulator by calibration.

4. The method of claim 1, further comprising:

providing a fixed elevated back pressure against which said first fluid flow stream is pumped to provide a reproducible flow source to a supercritical fluid system.

5. The method of claim 1, wherein:

said pump rate is controllable with variable flow rates when pumping against said elevated pressure in said first fluid flow stream.

6. The method of claim 1, wherein:

said method is operated under approximate isocratic conditions.

7. A method for converting a pump for use in a combined flow stream containing a mixture of highly compressed gas, compressible liquid or supercritical fluid; and a relatively incompressible liquid, comprising:

controlling inlet pressure to a pump of a first flow stream of a highly compressed gas, compressible liquid or supercritical fluid;

controlling temperature of said first flow stream;

pumping of said first flow stream, consisting of a pure fluid, against an elevated pressure rate resulting in delivery of a controllable flow rate of said first flow stream at a constant compressibility compensation without the need for dynamically compensating said pump for compressibility changes in said first flow stream.

8. The method of claim 7, wherein:

said pump is operated at variable flow rates when pumping against said elevated pressure in said first fluid flow stream.

9. The method of claim 7, further comprising:

providing a fixed elevated back pressure against which said first fluid flow stream is pumped to provide a reproducible flow source to a supercritical fluid system.

10. The method of claim 7, wherein:

said elevated pressure after said outlet of said pump is accomplished by delivering said first fluid flow stream from said pump against a back pressure regulator valve installed in said flow stream downstream of said pump and upstream from the joining of said first flow stream with said second fluid flow stream.

11. The method of claim 7, wherein:

said method is operated under approximate isocratic conditions.

12. The method of claim 7, further comprising the step of:

determining the flowrate of said first flow stream after said elevated pressure by calibration.

* * * * *